(12) United States Patent
Pastrana-Rios et al.

(10) Patent No.: US 9,702,810 B1
(45) Date of Patent: Jul. 11, 2017

(54) DUAL CELL HOLDER SYSTEM

(71) Applicants: Belinda Pastrana-Rios, Rincon, PR (US); Nicolas Esteves, Mayaguez, PR (US); José Javier Rodriguez-Toro, Mayaguez, PR (US)

(72) Inventors: Belinda Pastrana-Rios, Rincon, PR (US); Nicolas Esteves, Mayaguez, PR (US); José Javier Rodriguez-Toro, Mayaguez, PR (US)

(73) Assignee: University of Puerto Rico, San Juan, PR (US)

( * ) Notice: Subject to any disclaimer, the term of this patent is extended or adjusted under 35 U.S.C. 154(b) by 95 days.

(21) Appl. No.: 14/492,093

(22) Filed: Sep. 22, 2014

(51) Int. Cl.
| | | |
|---|---|---|
| *B01L 9/06* | (2006.01) | |
| *G01N 21/01* | (2006.01) | |
| *G01N 21/35* | (2014.01) | |

(52) U.S. Cl.
CPC ............. *G01N 21/01* (2013.01); *G01N 21/35* (2013.01); *G01N 2021/3595* (2013.01); *G01N 2201/02* (2013.01)

(58) Field of Classification Search
CPC .............. B01L 9/00; B01L 9/06; G01N 21/01
USPC ......................................... 422/560, 561, 562
See application file for complete search history.

(56) References Cited

U.S. PATENT DOCUMENTS

| | | | | |
|---|---|---|---|---|
| 5,808,020 | A * | 9/1998 | Ferrieri | B01J 19/0006 204/157.15 |
| 6,599,484 | B1 * | 7/2003 | Zigler | G01N 35/1079 422/129 |
| 8,355,132 | B2 * | 1/2013 | Xia | B01L 9/06 250/432 R |

* cited by examiner

*Primary Examiner* — Jill Warden
*Assistant Examiner* — Dwayne K Handy
(74) *Attorney, Agent, or Firm* — Hoglund & Pamias, PSC; Robert J. Rios (57) ABSTRACT

The invention provides a dual cell holder system that allows for the identical match of temperature conditions for both sample and reference simultaneously by providing two cells and a dual cell holder. The system is heated by a heating element and cooled by a Peltier, thus eliminating a significant source of humidity and the potential for leak from a water-cooling device or any of its hoses.

17 Claims, 11 Drawing Sheets

DUAL CELL HOLDER SYSTEM

BACKGROUND OF THE INVENTION

The protein aggregation phenomena are prevalent throughout the industrial bioprocess. Proteins are expensive to express, isolate and purify due to their complex physical-chemical characteristics. Aggregation is considered a primary mode of protein degradation, often leading to immunogenicity in patients and a loss of efficacy. That is why the detection and determination of protein aggregates is a key point in the biopharmaceutical industry, as well as, in scientific research. The formation of protein aggregates is critical in industrial applications, because they can highly affect the production of protein therapeutics (i.e., biologics or biosimilars) effectively lowering the production yields.

Figure 11:
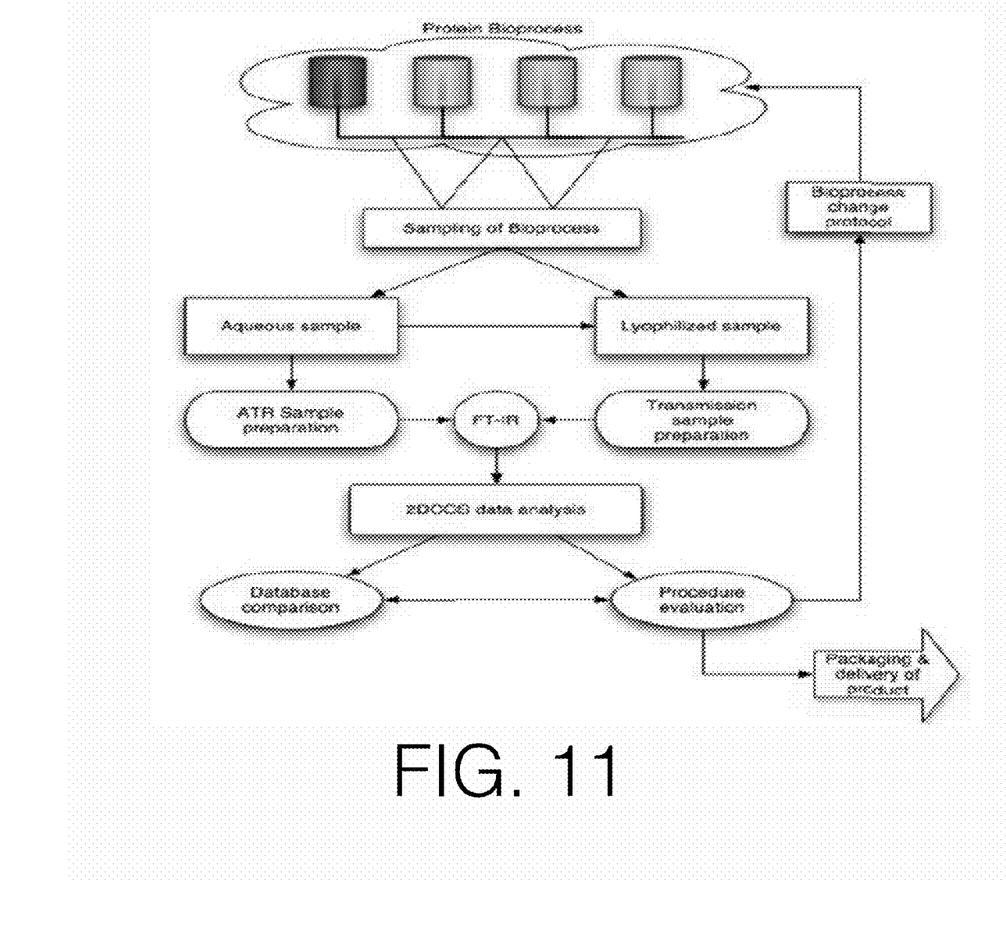
FIG. 11 illustrates the phases of a protein bioprocess.

U.S. Pat. No. 8,268,628 by Pastrana et al., teaches a method for determining the mechanism of aggregation and the amount of aggregation in protein, peptide or peptoid formulation, in solution or lyophilized state without the use of probes or additives by performing a novel FT-IR and 2DCOS analysis. FT-IR spectroscopy allows for a high degree of flexibility and speed in the determination of protein aggregates, with limited manipulation and without the use of exogenous probes. According to the '628 method, a sample is heated and left to equilibrate followed by spectral acquisition at the desired temperature and by following the method described by the '628 patent the determination of protein, peptide and peptoid, stability, aggregation and viability can be performed. The method has been applied to the study of lipids, membrane proteins, hydrophilic proteins, peptides and peptoids as a single component or in binary or ternary mixtures with other peptides, or lipid mixtures. When studying two protein components in a mixture or complex, one of the components must be isotopically labeled to allow for the simultaneous detection of each component. The flexibility of sample preparation, its potential for automation and data analysis are key elements of value for pharmaceutical protein formulation as illustrated in FIG. 11.

More specifically, the method described in the '628 patent uses FT-IR spectroscopy combined with the two-dimensional correlation analysis (2DCOS) which allows for the determination of the presence of aggregates, the determination of the mechanism of aggregation, allowing for correction in the pipeline manufacturing process of the protein to once again generate viable protein. In addition, the thermal transition of the protein can also be determined and a 2DCOS plot generated to compare with the established viable protein, allowing for quality control, stability and viability of the desired protein product. The ease of sample preparation and data analysis allows for the automation of this method.

However, FT-IR accessories for thermal dependence studies where both reference and sample are under identical temperature conditions are not commercially available. Normally, a user would have to perform the analysis of the reference then the sample and at times also collect water vapor spectra and perform tedious data manipulation.

Thus, there is a long felt need in the art for an FT-IR accessory suitable for thermal dependence studies where both reference and sample are maintained under identical temperature conditions.

SUMMARY OF THE INVENTION

The invention provides a dual cell holder system that allows for the identical match of temperature conditions for both sample and reference.

According to an aspect of the invention, a dual cell holder system allows for the identical match of temperature conditions for both sample and reference for a stepwise shuttling between reference and sample during spectral data acquisition.

According to another aspect of the invention, a dual cell holder enhances the capability of: matching the desired temperature conditions for sample and reference, the instrument response, the detector response, and humidity conditions resulting in a significant improvement in the acquired spectral data quality with minimal data manipulation and baseline correction.

According to still another aspect of the invention, the time required for data analysis is dramatically reduced.

According to one aspect of the invention, the time saved in data manipulation can be invested in increased data acquisition times to enhance S/N ratio by increasing the number of scans.

According to another aspect of the invention, the device is heated by a heating element and cooled by a Peltier, thus eliminating a significant source of humidity (i.e., water bath) and the potential for leak from the water-cooling device or any of its hoses.

According to still another aspect of the invention, an interface is provided to allow for programming the method so as to run fully automated without the need of a user.

According to yet another aspect of the invention, the dual cell holder system is not limited to analyzing proteins, peptides or peptoids as described for example in the '628 patent mentioned above, but may be used to analyze any liquid sample, lipid, or polymers during a thermal perturbation.

According to one aspect of the invention, the dual cell holder can be applied to the study of substances (organic or inorganic), materials or reagents, and liquids in general.

According to another aspect of the invention, the dual cell holder can be used in spectrophotometers where a shuttle or automated method of sampling is used.

According to still another aspect of the invention, the use of the dual cell holder is not limited to the infrared range, but can also be used in UV and visible range, circular dichroism (CD), vibrational circular dichroism, and Raman spectroscopies for the characterization of different materials and substances or excipients.

According to yet another aspect of the invention, the device for the FT-IR accessory is a self-contained demountable cell with a fixed path length that will not leak According to one aspect of the invention, the dual cell holder is easily used with several thermal couples for accurate temperature reading, a single heating element and Peltier cooling system.

According to another aspect of the invention, the dual cell holder allows the sample and the reference to have similar temperature gradient and temperature equilibrium conditions making it ideal for protein analysis.

According to still another aspect of the invention, the samples that may be analyzed are not limited to proteins. Other excipients, such as liquids, organics or inorganic materials or reagents can also be analyzed within the temperature range limitations of the device of the invention.

BRIEF DESCRIPTION OF THE DRAWINGS

Further features and advantages of the invention will become apparent from the following detailed description taken in conjunction with the accompanying figures showing illustrative embodiments of the invention, in which.

Throughout the figures, the same reference numbers and characters, unless otherwise stated, are used to denote like elements, components, portions or features of the illustrated embodiments. The subject invention will be described in detail in conjunction with the accompanying figures, in view of the illustrative embodiments.

DETAILED DESCRIPTION OF THE INVENTION

Figure 1:
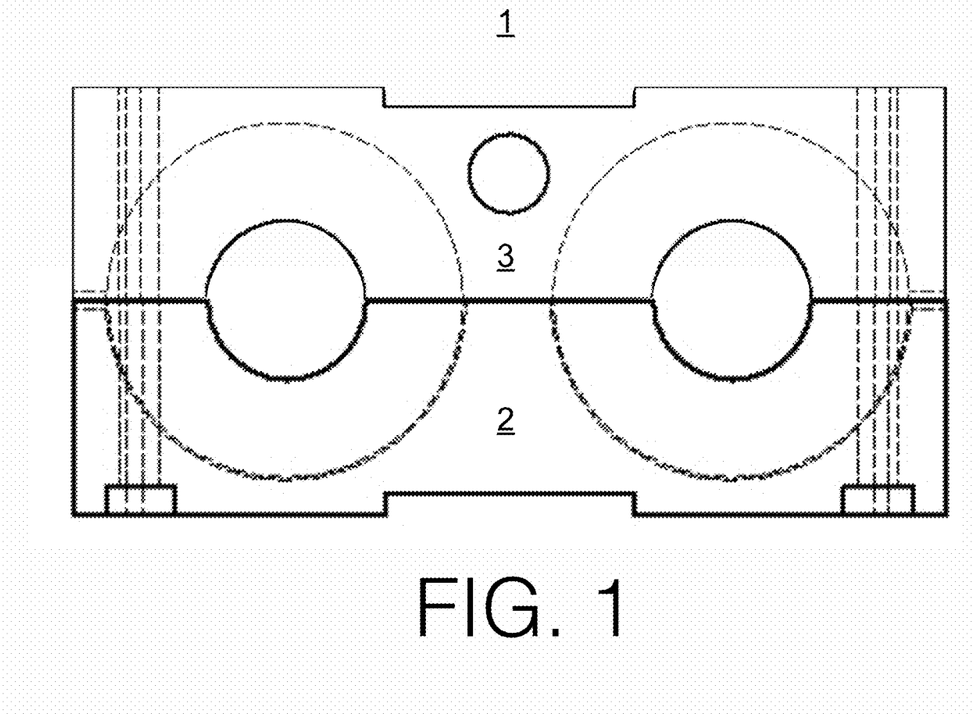
FIG. 1 shows a front view of the dual cell holder, according to the present invention.

The dual cell holder system of the present invention comprises a substantially symmetrical dual cell holder 1 having two interlocking parts, top part 3 and a bottom part 2 as shown in FIG. 1. As can be seen, the dual cell holder 1 is designed to provide separate areas for positioning within both a sample and a reference at the appropriate distance from each other as required by a spectrometer. The shape and configuration of the dual cell holder 1 allows for the use of both active cooling and heating components.

Figure 2A:
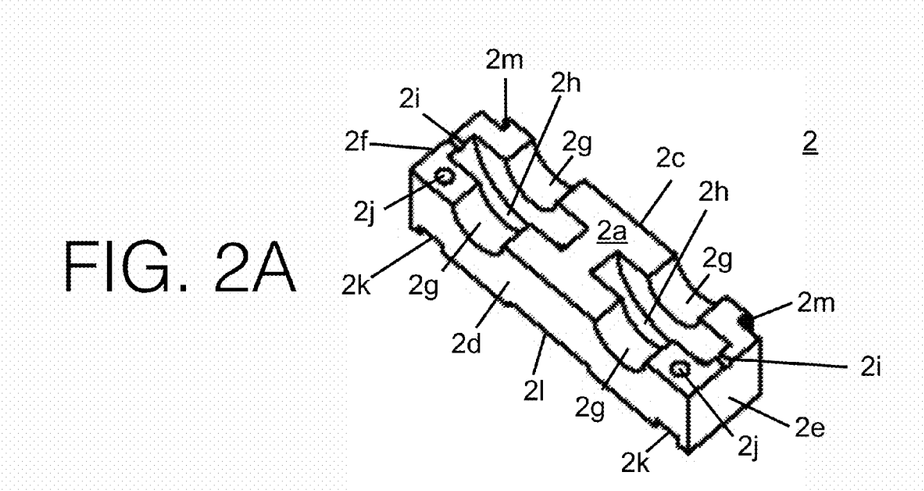
FIG. 2A shows a top perspective view of a bottom part of the dual cell holder, according to the present invention.
Figure 2B:
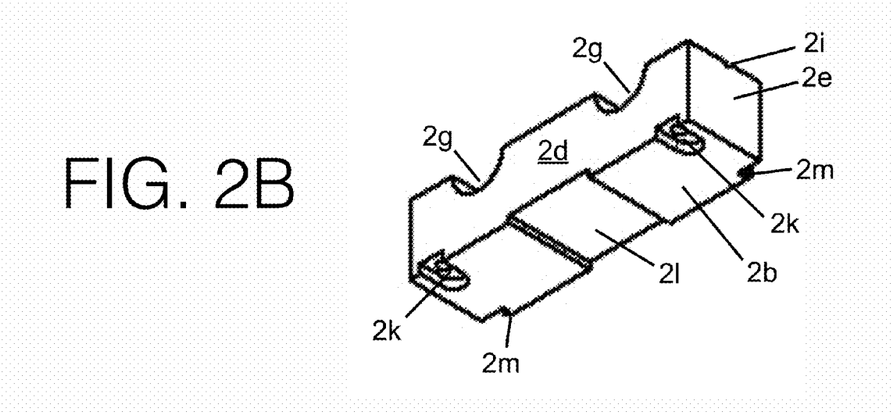
FIG. 2B shows a bottom perspective view of a bottom part of the dual cell holder, according to the present invention.
Figure 3A:
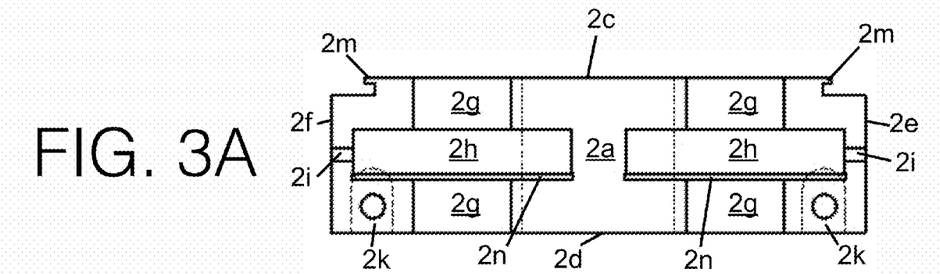
FIG. 3A shows a top view of a bottom part of the dual cell holder, according to the present invention.
Figure 3B:
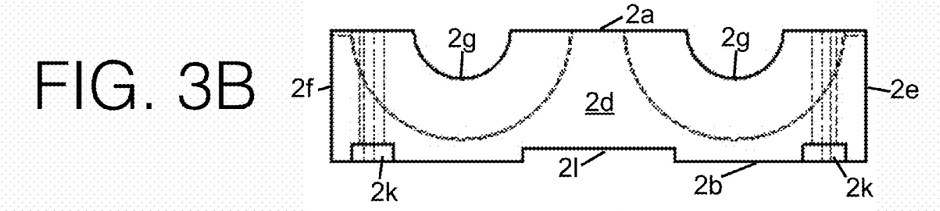
FIG. 3B shows a front view of a bottom part of the dual cell holder, according to the present invention.
Figure 3C:
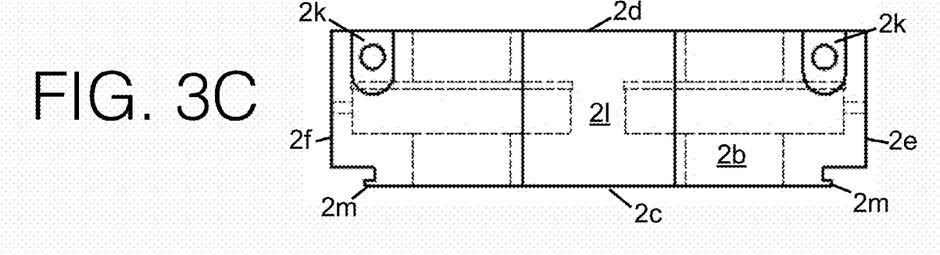
FIG. 3C shows a bottom view of a bottom part of the dual cell holder, according to the present invention.
Figure 10:
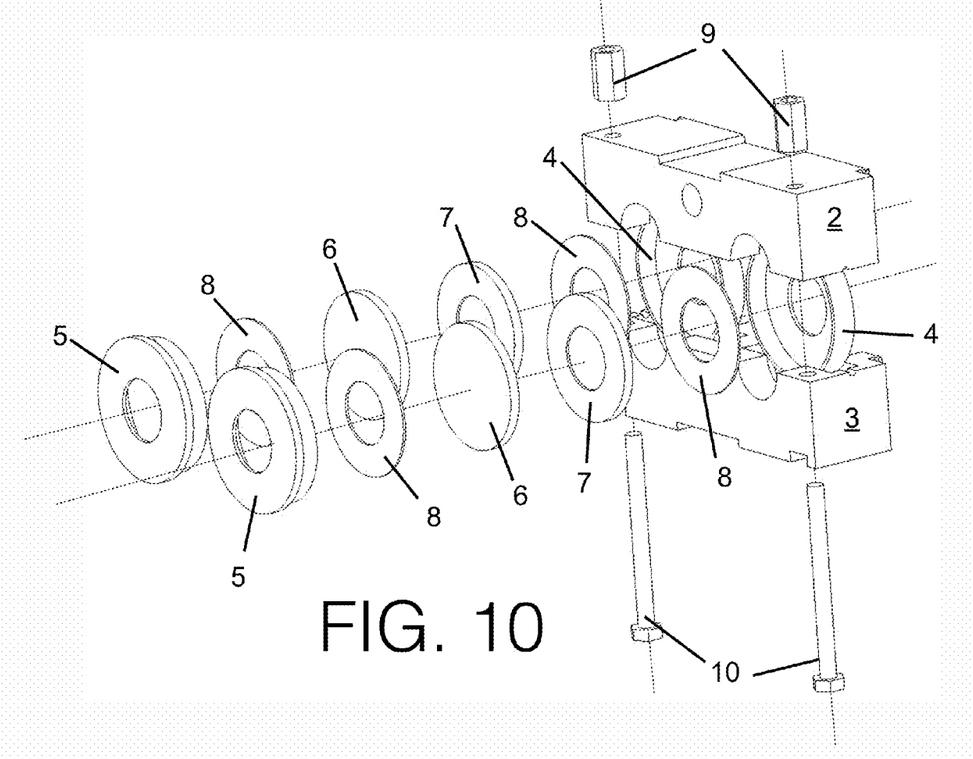
FIG. 10 shows an exploded perspective view of the dual cell holder system, according to the present invention.

The bottom part 2 of the dual cell holder 1 is further illustrated in FIGS. 2A, 2B, 3A, 3B and 3C. The bottom part 2 is divided into two separate portions each one having a separate recessed receiving area 2h configured to receive the cell having either the reference or the sample. A solid middle section having a top surface 2a is provided to separate both receiving areas 2h. Each receiving area of the bottom part 2 is provided with front and back openings configured in the preferred embodiment as semi-circular openings 2g coaxially aligned with its respective receiving area 2h. As will be explained later in detail, these openings 2g are provided to allow an IR beam to have unobstructed access to the windows containing the reference and sample enclosed within the respective cells which in turn, are positioned inside the receiving areas 2h. Guiding elements 2m are provided on the lateral sides of a back surface 2c so that when interlocked with the top part 3 the dual cell holder 1 is easily mounted on an existing sample shuttle of an FT-IR sample compartment. An opening 2i are provided on each side 2e and 2f of the bottom part as shown in FIGS. 2A and 3A. These openings 2i are provided to allow unobstructed insertion of a temperature sensor such as a thermocouple that will contact the sample and reference for accurate temperature measurements. A bottom surface 2b of the bottom part 2 is provided with a recessed portion 2l configured to receive a cooling element for cooling the dual cell holder 1. In a preferred embodiment of the invention, the cooling element is a Peltier element having a shape configured to match and to snuggly fit inside said recessed portion 2l. A pass-through aligning opening is also provided on each side of the bottom part 2, wherein one end 2j of the pass-through opening is located on the top surface 2a and the other end 2k of said pass-through opening is located on the bottom surface 2b. These pass-through aligning openings are provided to receive a set of screws 10 that will provide proper alignment when the bottom part 2 is interlocked with the top part 3 the dual cell holder 1. Also, the set of screws 10 can be used to fasten or clamp the top and bottom part together by means of nuts 9 as shown in FIG. 10.

Figure 4A:
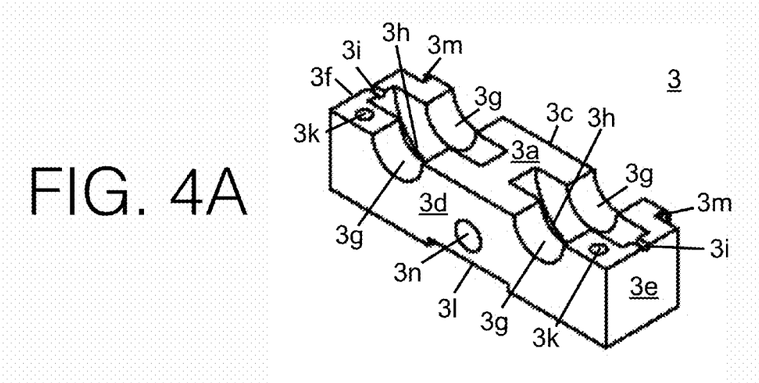
FIG. 4A shows a top perspective view of a top part of the dual cell holder, according to the present invention.
Figure 4B:
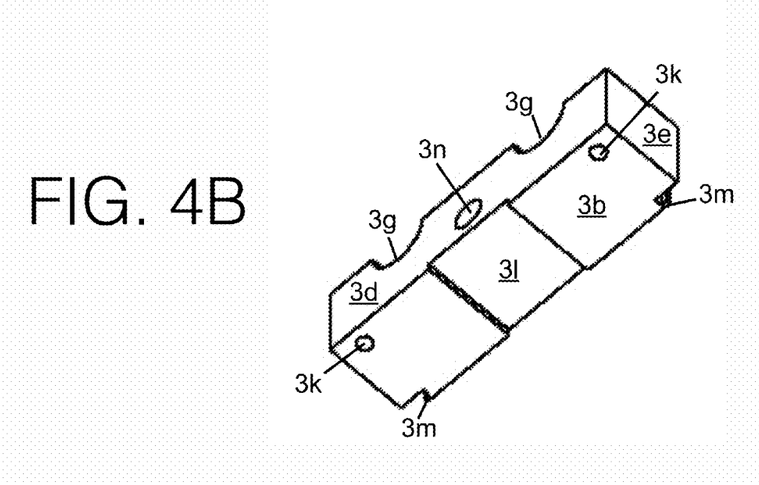
FIG. 4B shows a bottom perspective view of a top part of the dual cell holder, according to the present invention.
Figure 5A:
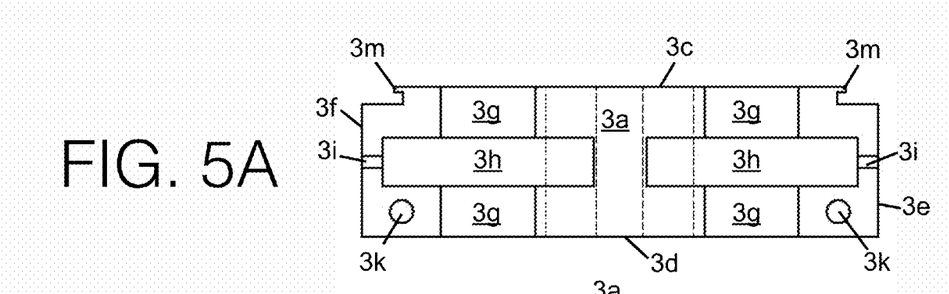
FIG. 5A shows a top view of a top part of the dual cell holder, according to the present invention.
Figure 5B:
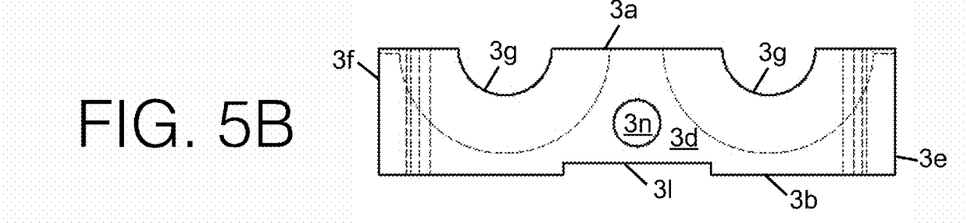
FIG. 5B shows a front view of a top part of the dual cell holder, according to the present invention.
Figure 5C:
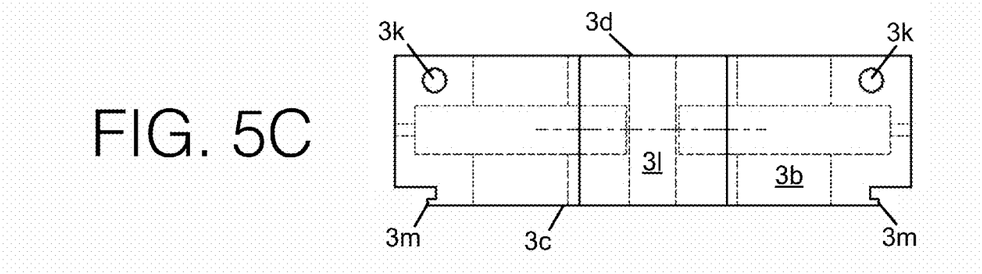
FIG. 5C shows a bottom view of a top part of the dual cell holder, according to the present invention.
Figure 6A:
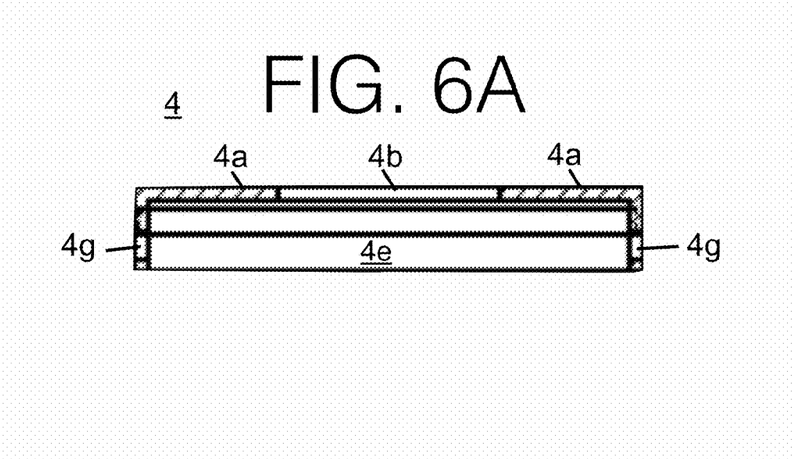
FIG. 6A shows a cross-sectional view of a top part of a cell, according to the present invention.
Figure 6B:
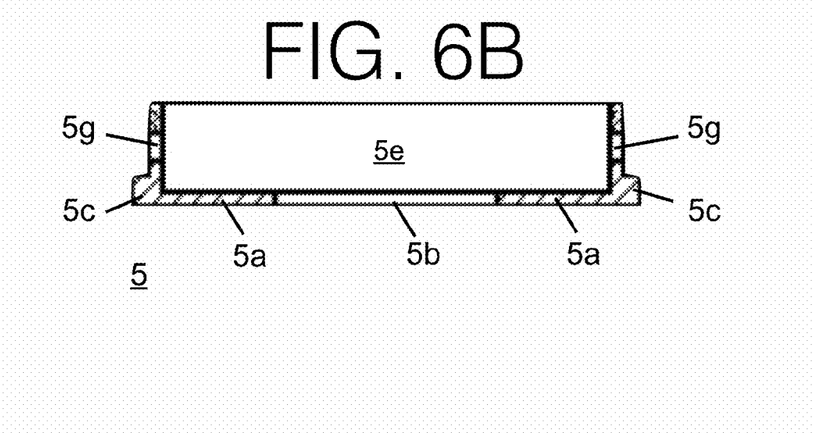
FIG. 6B shows a cross-sectional view of a bottom part of a cell, according to the present invention.
Figure 6C:
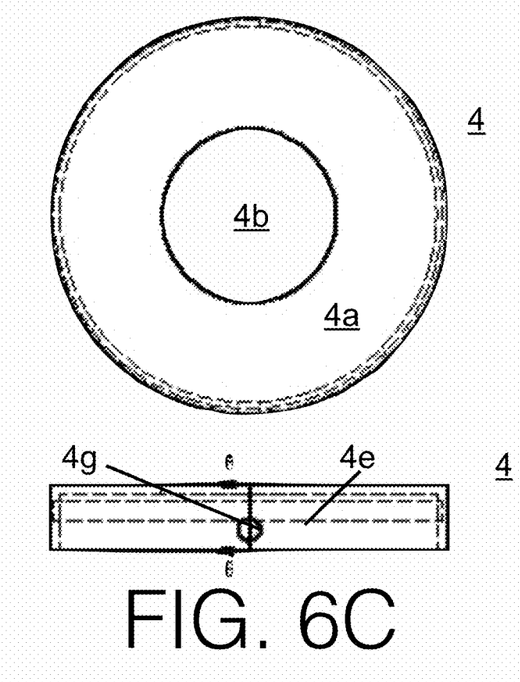
FIG. 6C shows another view of a top part of a cell, according to the present invention.
Figure 6D:
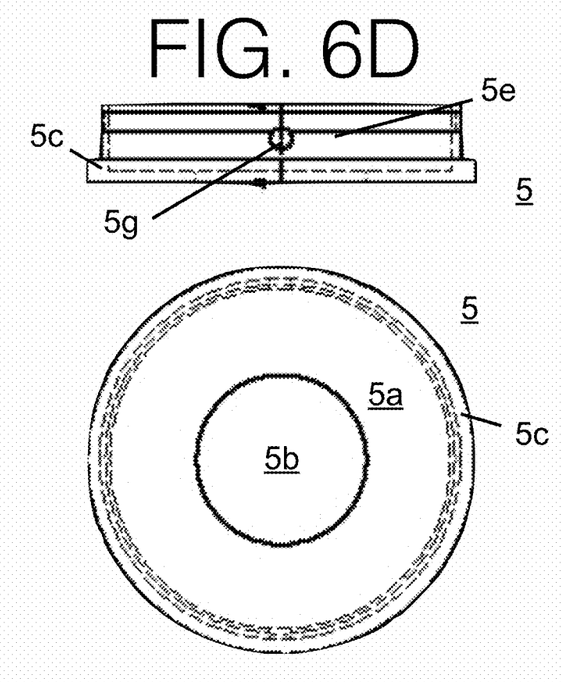
FIG. 6D shows another view of a bottom part of a cell, according to the present invention.

The top part 3 of the dual cell holder 1 is further illustrated in FIGS. 4A, 4B, 5A, 5B and 5C. As will be evident the configuration of the top part 3 is similar and symmetrical to the configuration of the bottom part 2 with the exception of some elements or portions that will be explained in detail below. The top part 3 is also divided into two separate portions each one having a separate recessed receiving area 3h configured to receive the cell having either the reference or the sample. A solid middle section having a top surface 3a is provided to separate both receiving areas 3h. Each receiving area of the top part 3 is provided with front and back openings configured in the preferred embodiment as semi-circular openings 3g coaxially aligned with its respective receiving area 3h. These openings 3g are provided to allow an IR beam to have unobstructed access to the windows containing the reference and sample enclosed within the respective cells which in turn, are positioned inside the receiving areas 3h. Guiding elements 3m are provided on the lateral sides of a back surface 3c so that when interlocked with the bottom part 2 the dual cell holder 1 is easily mounted on an existing sample shuttle of an FT-IR sample compartment. An opening 3i are provided on each side 3e and 3f of the top part 3 as shown in FIGS. 4A and 5A. These openings 3i are provided to allow unobstructed insertion of a temperature sensor such as a thermocouple that will contact the sample and reference for accurate temperature measurements. A bottom surface 3b of the top part 3 is also provided with a recessed portion 3l configured to receive a cooling element for cooling the dual cell holder 1. A pass-through opening 3n passing through said top part 3 from a front surface 3d to a back surface 3c is provided to receive a heating element for heating the dual cell holder 1. A pass-through aligning opening is also provided on each side of the top part 3, wherein one end 3k of the pass-through aligning opening is located on the top surface 3a and the other end 3k of said pass-through aligning opening is located on the bottom surface 3b. These pass-through aligning openings are provided to receive a set of screws 10 that will provide proper alignment when the bottom part 2 is interlocked with the top part 3 of the dual cell holder 1 as shown in FIG. 10.

The cell according to the invention is further illustrated in FIGS. 6A, 6B, 6C, and 6D. The cell of the invention comprises a pair of interlocking circular parts 4 and 5 configured to form a chamber that securely encases a set of optically transparent windows allowing for the spectroscopic analysis of the desired sample and reference. A part 4 comprises a lid configured to be cover a part 5 comprising a housing configured to receive the set of windows containing the sample or reference. A mating threaded mechanism is provided on both parts 4 and 5 to selectively close and tighten the cell of the invention. A pair of coaxially aligned port openings 4g are provided around the periphery of said part 4 providing unobstructed access to an interior area 4e of said part 4. A pair of coaxially aligned port openings 5g are also provided around the periphery of said part 5 providing unobstructed access to an interior area 5e of said part 5. In operation, part 4 is positioned on top of said part 5 serving as a lid that is tighten until the set of port openings 4g are coaxially aligned with the set of port openings 5g of the part 5 so a temperature sensor is inserted into an interior area defined by the interior areas 4e and 5e for contacting the set of windows containing the sample or reference for measurement purposes. The part 4 further comprises a round opening 4b centrally positioned on a top surface 4a of the part 4. The part 5 further comprises a round opening 5b centrally positioned on a bottom surface 5a of the part 5. In operation, part 4 is positioned on top of said part 5 so that the round opening 4b is coaxially aligned with the round opening 5b of said part 5 to allow an IR beam to have unobstructed access to the windows containing the reference and sample enclosed within the respective cells.

Figure 7:
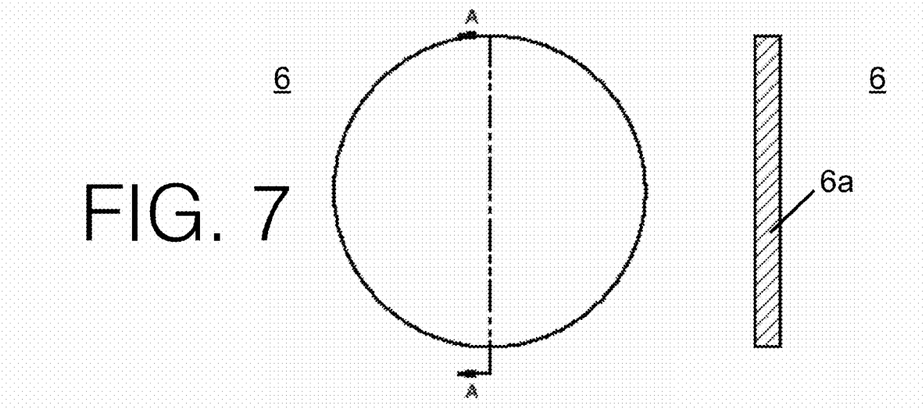
FIG. 7 shows a window, according to the present invention.
Figure 8:
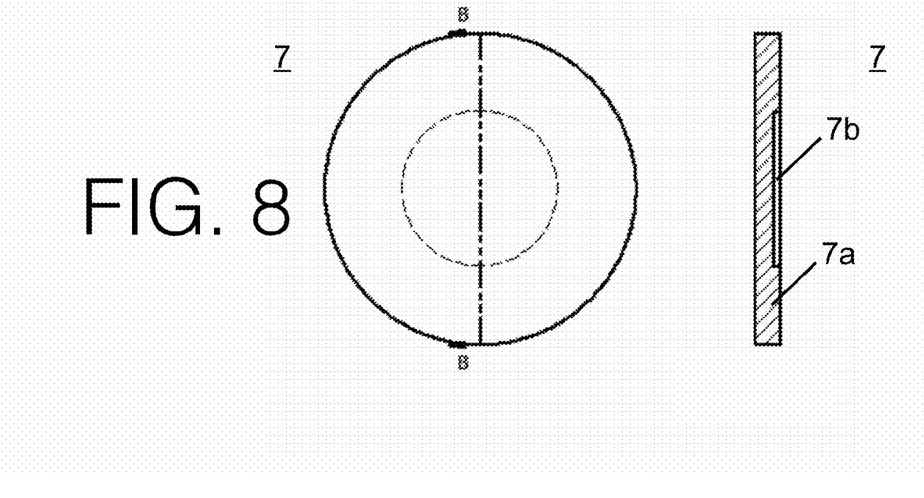
FIG. 8 shows another window with the sample, according to the present invention.

FIGS. 7 and 8 illustrates the set of windows according to the present invention. A first window comprises an optically transparent window 6a and a second window comprises an optically transparent window 7a having a receiving portion 7b containing the sample or reference.

Figure 9:
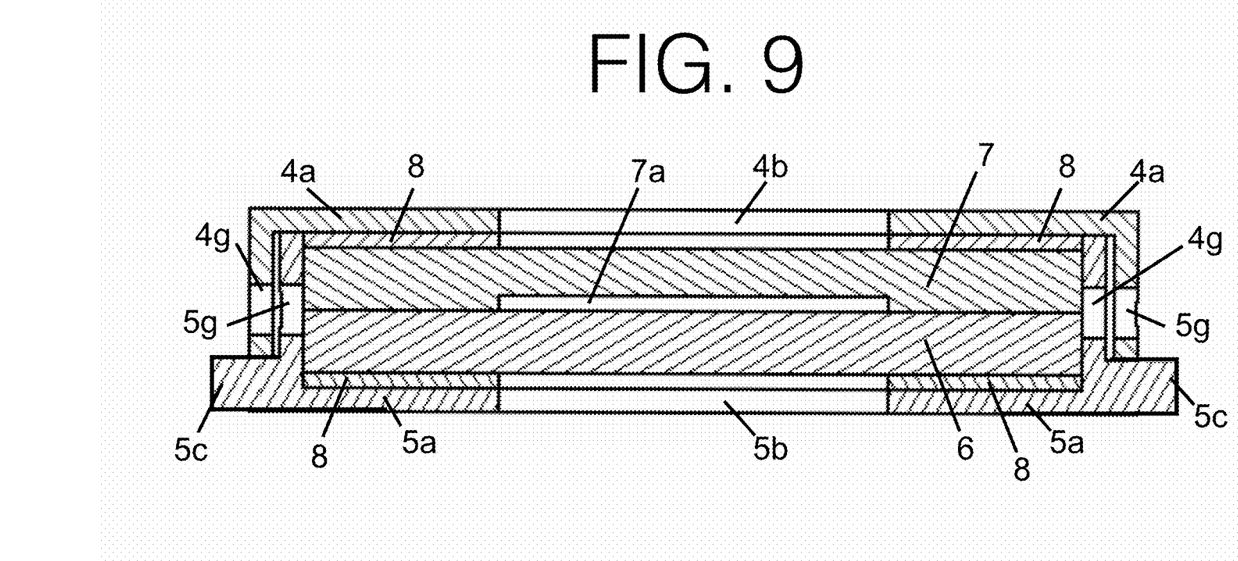
FIG. 9 shows a cross-sectional view of the cell enclosing the sample, according to the present invention.

FIGS. 9 and 10 illustrates the complete cell containing the reference/sample and the dual cell holder of the invention in conjunction with said cell, respectively. The set of windows containing the sample/reference is positioned inside the part 5, wherein a spacer 8 is also provide to ensure proper distance, alignment and securely position said windows within the cell. If needed a second spacer 8 could be provided or alternatively no spacer could be used. As can be seen, openings 4g and 5g are coaxially aligned to allow unobstructed access and contact with said windows 6 and 7.

In operation, once the reference and sample cells are prepared as illustrated in FIG. 9 each cell is inserted into the respective receiving areas 2h of the bottom part 2. A retaining portion 2n is provided on each receiving area 2h so that a retaining tab 5c located on the bottom surface 5a of the cell is inserted and received inside said retaining portion 2n allowing said cell to be inserted in a single direction with respect to said receiving areas 2h. Screws 10 are inserted into the aligning pass-through openings and are secured with nuts to maintain the parts 4 and 5 aligned during the installation process. Once the cells are positioned within the receiving areas, the cells are moved to ensure that the openings 4g and 5g are also coaxially aligned with openings 2i and 3i to allow insertion of a temperature sensor as previously explained. After all the openings are coaxially aligned the interlocking parts 4 and 5 are secured by the set of screws 10 and nuts 9 so that the dual cell holder is mounted into the machine by means of the guiding elements 2m and 3m. The Peltier element is positioned in contact with the recessed portion 2l or 3l and the heating element is inserted into the pass-through opening 3n.

The dual cell holder system of the present invention comprises two cells and a dual cell holder that are made of materials such as Aluminum or anodized Aluminum that effectively allow heat transfer to and from the sample and reference inside the cells. The cell of the invention comprises two interlocking parts containing a center hole with a preferred width of 2.5 cm to allow for the IR beam to access said sample and reference.

In order to provide an identical match of temperature conditions for both sample and reference for analysis the dual cell holder system of the present invention is used with additional components. An Ambient Temperature Controller is used to provide feedback about ambient temperature. A Contact Temperature Sensor is used to provide feedback about the cell holder temperature. A Heater element is used to apply heat energy to the cell holder. A Heater control circuit provides the required signals and power to the Heater element. A Thermoelectric element is used to remove heat energy from the cell holder. A Thermoelectric circuit is used to provide the required signals and power to the thermoelectric element. A Temperature Controller is provided to manage the thermoelectric control circuit and the heater element control circuit. The Controller takes decisions based on mathematical models to provide temperature control. A Communications System provides communication between the Temperature Controller and the Test System. It also keeps the synchronization of the operation between the systems. A Security System verifies operation parameters and interrupts power to the system in case the operation parameters turn dangerous.

In accordance with a method for accurate temperature control and sensing, the Temperature Controller receives the parameters of operation from the Communications System and saves it to an internal memory. The Temperature Controller loads any previously used operating corrections and sends a ready signal to the Communications System which in turns sends a start signal to the Temperature controller. The Temperature Controller starts a temperature feedback monitoring process where the current temperature is read and compared with a target temperature. A selection between a heating and cooling operation as well as the intensity of the operation is determined based on the comparison. The previous step is repeated periodically until a target temperature is reached. After completing a configurable stabilization period a ready signal is sent to the Communications Controller. This whole process is repeated until the test recipe is done and the Communication System sends an experiment done signal. Afterwards, the Temperature Controller verifies the temperature of the cell holder and applies any correction necessary for safe handling of the cell holder. The device of the present invention may be used for both qualitative and quantitative determination of the desired sample. The device allows for the use of different windows and path lengths enclosed in a cell. The device allows for accurate temperature control of both sample and reference simultaneously.

Although the present invention has been described herein with reference to the foregoing exemplary embodiment, this embodiment does not serve to limit the scope of the present invention. Accordingly, those skilled in the art to which the present invention pertains will appreciate that various modifications are possible, without departing from the technical spirit of the present invention.

We claim:
1. A dual-cell holder system comprising:
a cell holder having:
a first cell receiving cavity configured to receive a first cell and having a first dent configured to receive a protrusion of said first cell, a first temperature measuring port configured as a first opening allowing insertion of a first temperature measuring device into said first cell receiving cavity and a first pass-through opening configured to allow access into said first cell receiving cavity;
a second cell receiving cavity configured to receive a second cell and having a second dent configured to receive a protrusion of said second cell, a second temperature measuring port configured as a second opening allowing insertion of a second temperature measuring device into said second cell receiving cavity and a second pass-through opening configured to allow access into said second cell receiving cavity, wherein said second cell receiving cavity is positioned side-by-side with said first cell receiving cavity;
a heating element port configured as an opening allowing insertion a heating element into said cell holder; and
a cooling element port configured as depression on a surface of said dual-cell holder allowing a cooling element to fixedly contact said cell holder;
said cell holder comprises a first piece and a second piece removably attached to said first piece, wherein said first piece further comprises first aligning pass-through holes and said second piece further comprises second aligning pass-through holes, said first aligning pass-through holes and said second aligning pass-through holes are configured to match with each other for receiving aligning elements and wherein said cell holder further comprises a set of screws and nuts that secure said first piece to said second piece and allow aligning said first piece with said second piece when attaching said first piece to said second piece.

2. The dual-cell holder system of claim 1, wherein said first piece is removable attached on top of said second piece.

3. The dual-cell holder system of claim 1, wherein a first portion of said first cell receiving cavity is formed on said first piece and a second portion of said first cell receiving cavity is formed on said second piece; a first portion of said second cell receiving cavity is formed on said first piece and a second portion of said second cell receiving cavity is formed on said second piece so that said first cell receiving cavity and said second cell receiving cavity are completely enclosed within said cell holder when said first piece and said second piece are attached to each other.

4. The dual-cell holder system of claim 1, wherein a first portion of said first temperature measuring port is formed on said first piece and a second portion of said first temperature measuring port is formed on said second piece; a first portion of said second temperature measuring port is formed on said first piece and a second portion of said second temperature measuring port is formed on said second piece so that said first temperature measuring port and said second temperature measuring port are completely formed when said first piece and said second piece are attached to each other.

5. The dual-cell holder system of claim 1, wherein a first portion of said first pass-through opening is formed on said first piece and a second portion of said first pass-through opening is formed on said second piece; a first portion of said second pass-through opening is formed on said first piece and a second portion of said second pass-through opening is formed on said second piece so that said first pass-through opening and said second pass-through opening are completely formed when said first piece and said second piece are attached to each other.

6. The dual-cell holder system of claim 1, wherein said first dent and said second dent are formed on one of: said first piece and said second piece.

7. The dual-cell holder system of claim 1, wherein said first dent receives the protrusion.

8. The dual-cell holder system of claim 1, wherein said heating element port is formed on one of: said first piece and said second piece.

9. The dual-cell holder system of claim 1, wherein said cooling element port is formed on one of: said first piece and said second piece.

10. The dual-cell holder system of claim 1, wherein said aligning elements are used for attaching said first piece to said second piece.

11. The dual-cell holder system of claim 1, wherein each of said first cell and said second cell comprises:
a base element having a receiving area, a first pass-through opening for receiving a temperature measuring device into said receiving area, a second pass-through opening positioned perpendicular to said first pass-through opening to allow access into said receiving area and a protrusion extending outwardly from said base; and
a removable lid element attached to said base element to enclose said receiving area, a third pass-through opening for receiving said temperature measuring device into said receiving area, a fourth pass-through opening positioned perpendicular to said second pass-through opening to allow access into said receiving area, wherein said first pass-through opening and said third pass-through opening are coaxially aligned to each other and said second pass-through opening and said fourth pass-through opening are coaxially aligned to each other when said lid element is attached to said base element.

12. The dual-cell holder system of claim 11, wherein said first cell is positioned within said first cell receiving cavity so that the base protrusion of said first cell fits inside said first dent, said first pass-through opening on the base element of the first cell and said third pass-through opening on the lid element of the first cell are coaxially aligned with said first temperature measuring port; and said second cell is positioned within said second cell receiving cavity so that the base protrusion of said second cell fits inside said second dent, said first pass-through opening on the base element of the second cell and said third pass-through opening on the lid element of the second cell are coaxially aligned with said second temperature measuring port.

13. The dual-cell holder system of claim 11, wherein said first cell is positioned within said first cell receiving cavity so that said second pass-through opening on the base of the first cell and said fourth pass-through opening on the lid of the first cell are coaxially aligned with the first pass-through opening of said first cell receiving cavity; and said second cell is positioned within said second cell receiving cavity so that said second pass-through opening on the base of the second cell and said fourth pass-through opening on the lid of the second cell are coaxially aligned with the second pass-through opening of said second cell receiving cavity.

14. The dual-cell holder system of claim 1, wherein said first cell encloses a sample material and said second cell encloses a reference material.

15. The dual-cell holder system of claim 14, further comprising at least one spacer element positioned between said sample material and the interior surface of said first cell and at least one spacer element positioned between said reference material and the interior surface of said second cell.

16. The dual-cell holder system of claim 11, further comprising a first temperature measuring device inserted into said first temperature measuring port, said first pass-through opening on the base element of the first cell and said third pass-through opening on the lid element of the first cell allowing contact with said sample material; and a second temperature measuring device inserted into said second temperature measuring port, said first pass-through opening on the base element of the second cell and said third pass-through opening on the lid element of the second cell allowing contact with said reference material.

17. The dual-cell holder system of claim 1, further comprising a heating element inserted into said heating element port of said cell holder; and a cooling element in contact with said heating element port of said cell holder.

\* \* \* \* \*